United States Patent [19]

Petrucelli et al.

[11] Patent Number: 5,535,753
[45] Date of Patent: Jul. 16, 1996

[54] APPARATUS AND METHODS FOR THE NONINVASIVE MEASUREMENT OF CARDIOVASCULAR SYSTEM PARAMETERS

[75] Inventors: Steven P. Petrucelli, Cranbury; Walter Welkowitz, Metuchen; Lisa K. Liss, Dunellen; Alan M. Smith, East Brunswick; Stephen A. Orbine, III, Bernardsville, all of N.J.

[73] Assignee: Rutgers University, New Brunswick, N.J.

[21] Appl. No.: 317,927

[22] Filed: Oct. 4, 1994

[51] Int. Cl.⁶ .................................................. A61B 5/00
[52] U.S. Cl. .......................... 128/672; 128/671; 128/713; 128/668; 128/687
[58] Field of Search .................................... 128/668, 670, 128/672, 687, 690–694, 702, 661.08

[56] References Cited

U.S. PATENT DOCUMENTS

| | | | |
|---|---|---|---|
| 4,899,758 | 2/1990 | Finkelstein et al. | 128/672 |
| 4,993,420 | 2/1991 | Welkowitz et al. | |
| 5,054,493 | 10/1991 | Cohn et al. | 128/672 |
| 5,101,828 | 4/1992 | Welkowitz et al. | |
| 5,211,177 | 5/1993 | Chesney et al. | |
| 5,316,004 | 5/1994 | Chesney et al. | 128/668 |
| 5,400,793 | 3/1995 | Wesseling | 128/691 |

OTHER PUBLICATIONS

M. Yelderman, "Continuous Measurement of Cardiac Output with the Use of Stochastic System Identification Techniques", J. Clin. Monit 6:322–332, 1990.

"Physiology", Berne, R. M. and Levy, M. N. copyright 1993 by C. V. Mosby Co.

*Primary Examiner*—Angela D. Sykes
*Assistant Examiner*—Robert L. Nasser, Jr.
*Attorney, Agent, or Firm*—Plevy & Associates

[57] ABSTRACT

Apparatus and methods for noninvasively measuring cardiovascular system parameters. According to a first preferred embodiment, the apparatus generates a time varying electrical voltage waveform having voltages corresponding to systolic and diastolic arterial pressures of the subject, the parameters being modelled by a lumped element electric circuit model analogous to the living subject's cardiovascular system, said circuit model including a systolic capacitor analogous to arterial compliance during systole, said apparatus comprising means for computing the value of said systolic capacitor from a measurement of an elapsed time between two voltage levels within a portion of said voltage waveform corresponding to systole, according to a predetermined criteria; and means for computing at least one said cardiovascular system parameter from said capacitor value. According to a second embodiment, a time-varying systolic arterial compliance is measured by measuring an arterial pulse pressure waveform. A third embodiment discloses a method of measuring cardiac output noninvasively from a cuff measurement of a patient's systolic minus diastolic blood pressure and a heart rate measurement. Cardiac output equations are derived from an unmodified Windkessel circuit model which models arterial compliance as a single lumped capacitance. General formulas for the value of the lumped capacitance are provided which are used to more accurately compute cardiac output from this circuit model.

15 Claims, 10 Drawing Sheets

APPARATUS AND METHODS FOR THE NONINVASIVE MEASUREMENT OF CARDIOVASCULAR SYSTEM PARAMETERS

FIELD OF THE INVENTION

This invention relates generally to the noninvasive measurement of cardiovascular system parameters, and in particular, to apparatus and methods for measuring cardiac output and arterial impedance parameters employing a single noninvasive transducer.

BACKGROUND OF THE INVENTION

Accurate noninvasive methods to measure cardiac output and arterial impedance parameters have been sought as an alternative to invasive catheter techniques with the associated patient discomfort and undesirable surgical procedure. Noninvasive techniques have been developed to predict arterial system impedance parameters which are based on electric circuit models of the arterial system. The circuit models are used in conjunction with pulse pressure waveform measurements on patients to predict cardiac output, arterial compliance, and so on.

The relationship between pressure and flow in the arterial system is similar to the relationship between voltage and current in an electrical system. Analogs between the electrical system and the physiological system have been proposed so that electrical circuits can be used to model the behavior of the physiological system. For example, electrical current is analogous to blood flow; each represents the movement of a substance (electrons, blood) through a closed system. In each system, the flow can be induced by a driving force, which is the voltage or pressure, respectively. The amount of flow in each system is determined by the impedance characteristics. For instance, capacitance is analogous to the elasticity (or compliance) of an artery. A narrowing of a blood vessel is analogous to increased resistance. In addition, the differential equations used to describe the behavior of electrical voltage and current can be directly applied to the physiological system.

Cardiac output may be expressed as the product of heart rate times volume of blood pumped per beat of the heart. Thus, under conditions of a consistent heart rate and stroke volume, cardiac output (liters/min)=heart rate (beats/min)×stroke volume (liters/beat).

Cardiac output or blood flow is also directly proportional to mean blood pressure and is inversely proportional to the peripheral resistance of the arterial system through which the blood flows.

Several noninvasive methods based on equivalent circuit model theory have been developed in the prior art. U.S. Pat. No. 4,993,420, entitled "Method and Apparatus for Noninvasive Monitoring Dynamic Cardiac Performance", to Welkowitz et al., and assigned to Rutgers University, the assignee herein, discloses a noninvasive method and apparatus employing two pulse transducers—one for measuring a carotid pulse waveform and the other for measuring a femoral pulse waveform. The carotid pulse waveform is applied as a voltage to a simulated aorta circuit, and the circuit component values are varied to develop a waveform output best matching the femoral pulse electrical waveform. The simulated circuit is then considered to be a representative model of the aorta of the living subject. An input current waveform corresponding to the aortic flow is calculated from the model. The circuit model used employs lumped circuit elements.

U.S. Pat. No. 5,101,828, entitled "Methods and Apparatus for Noninvasive Monitoring of Dynamic Cardiac Performance", to W. Welkowitz et al., and assigned to Rutgers University, discloses a similar noninvasive apparatus and method. Two pulse transducers are again employed to measure carotid and femoral pulse waveforms. Arterial parameters are predicted using a tapered aorta hybrid circuit model. This is a nonuniform hybrid model which provides a removable representation of the pressure transfer function of the aorta. By measuring input (carotid) and output (femoral) pressure waveforms, and finding the optimal fit between the model and arterial data, the cardiac output is estimated. A disadvantage of the above-cited methods is that they require two pulse waveform measurements at different locations—the carotid and the femoral artery positions. In clinical practice, measurement of the femoral arterial pulse is difficult. As a result, the above techniques suffer from being clinically impractical. In addition, measuring two pulse waveforms as opposed to only one waveform adds complexity to the measurement and to the associated measurement circuitry.

U.S. Pat. No. 5,211,177 entitled "Vascular Impedance Measurement Instrument", to Chesney et al., discloses a noninvasive vascular impedance instrument which apparently operates with the use of only one pulse pressure transducer. A finger-cuff transducer unit is employed to measure arterial blood pressure and provide waveform data which is digitized and applied to a microprocessor. A modified Windkessel circuit model of the arterial system is utilized to predict cardiac output and mean arterial pressure. This circuit model includes proximal (aortic) and distal (brachial) pulse pressure and proximal and distal arterial compliance. The accuracy reported in this patent for the disclosed method in comparison to a standard based upon a thermodilution or dye dilution technique appears to be satisfactory.

Another prior art method of predicting cardiac output is based on an unmodified Windkessel circuit model of the arterial system which consists of a single lumped element capacitor C to model arterial compliance during systole. By measuring heart rate (HR) and systolic minus diastolic pressure (PP), cardiac output is determined by:

$$CO(L/min)=HR(beats/min) \times C(Farads) \times PP(mmHg) \times 0.133.$$

Thus it is possible to obtain a measurement of cardiac output without having to decipher an arterial pressure waveform. However, it has been found that using a constant value for the capacitance C renders this method inaccurate. It would therefore be desirable to derive a general formula for C which substantially enhances the accuracy of this approach.

It is an object of the present invention to provide a noninvasive apparatus and method to accurately predict cardiac output and arterial system parameters which employs a single pulse pressure transducer, preferably to measure the carotid pulse pressure waveform.

It is a further object of this invention to provide such apparatus and method that models arterial compliance as a capacitance having one value during the systolic upshoot and another value during the diastolic decay of the pulse pressure waveform.

It is an additional object of this invention to provide such apparatus and method that measures a time varying arterial compliance during systole.

It is another object of the present invention to provide a method of measuring cardiac output from a measurement of a patient's heart rate and systolic minus diastolic blood pressure.

SUMMARY OF THE INVENTION

The present invention is directed towards apparatus and methods for noninvasively measuring cardiovascular system parameters of a living subject. According to a first preferred embodiment, the apparatus generates a time varying electrical voltage waveform having voltages calibrated to systolic and diastolic arterial pressures of the subject, the parameters being modelled by a lumped element electric circuit model analogous to the living subject's cardiovascular system, said circuit model including a systolic capacitor analogous to arterial compliance during systole, said apparatus comprising means for computing the value of said systolic capacitor from a measurement of an elapsed time between two voltage levels within a portion of said voltage waveform corresponding to systole, according to a predetermined criteria; and means for computing at least one said cardiovascular system parameter from said capacitor value.

The circuit model in the first preferred embodiment is the "LICO" circuit model, or "Local Impedance, Compliance and Output", which consists of the series combination of a DC voltage source, a switch, a diode, an inductor, and a systolic capacitor during the systolic portion of the cardiac cycle. During diastole, the systolic capacitor is replaced with the series combination of a diastolic resistor and a diastolic capacitor. By measuring the elapsed time between the minimum and maximum pressure points on an arterial pressure pulse waveform during systole, a value for the systolic capacitor may be computed from which an analogous systolic arterial compliance is determined. Blood flow is determined from this time constant and the measured pressure values. Only a single pressure transducer is required to sense pressure pulse waveforms at a single arterial location, preferably the carotid artery.

According to a second embodiment of the present invention, a time-varying arterial compliance is measured by measuring an arterial pulse pressure waveform. This arterial compliance varies as a function of arterial compliance during systole and is determined from a measurement of the pulse pressure at desired time points during systole.

Yet another embodiment of the present invention is directed to a method of measuring cardiac output noninvasively from a cuff measurement of a patient's systolic minus diastolic blood pressure, and a heart rate measurement. Cardiac output equations are derived from an unmodified Windkessel circuit model which models arterial compliance as a single lumped capacitance. General formulas for the value of the lumped capacitance are provided which are used to more accurately compute cardiac output from this circuit model.

BRIEF DESCRIPTION OF THE DRAWINGS

For better understanding of the instant invention, reference is made to the following description of exemplary embodiments thereof, considered in conjunction with the accompanying drawings, in which.

DETAILED DESCRIPTION OF THE INVENTION

Figure 1:
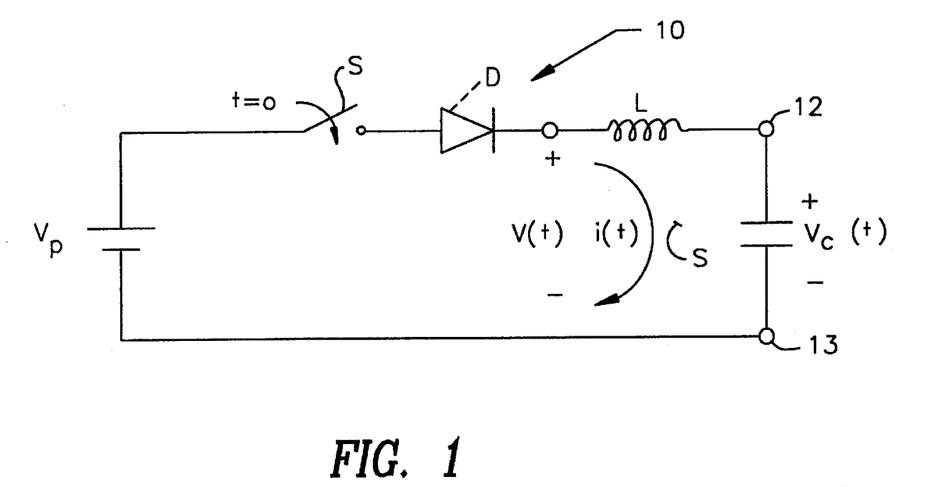
FIG. 1 is the LICO circuit model of the arterial system during systole according to the first embodiment of the present invention.
Figure 2:
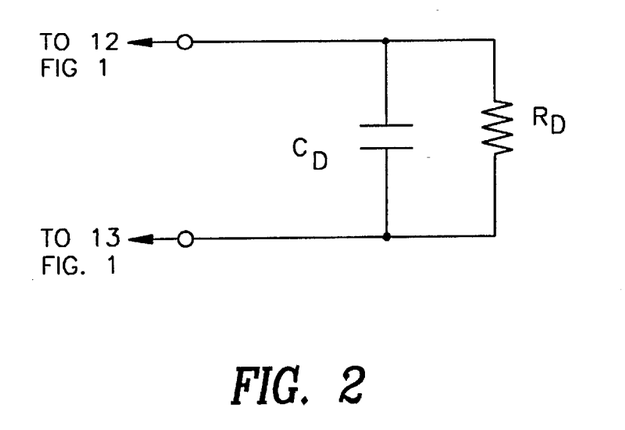
FIG. 2 is a portion of the LICO circuit model during diastole.

Referring to FIGS. 1 and 2, a circuit model 10 hereinafter referred to as the Local Impedance, Compliance and Output (LICO) circuit model, is used to predict cardiac output and arterial impedance parameters according to a first preferred embodiment of the present invention. Each circuit component of the LICO model 10 represents a parameter of the physiological system. The present invention employs algorithms which are based upon the LICO circuit model 10 to predict physiological parameters of a patient's arterial system from a measured arterial pressure pulse waveform, preferably from the carotid artery.

The circuit 10 of FIG. 1 is representative of the systolic portion of the cardiac cycle. The current i(t) is analogous to the blood flow from the heart's left ventricle to the aorta during systole. A switch S represents the opening and closing of the aortic valve, which marks the beginning and end of systole, respectively. The pressure within the heart's left ventricle is represented by the voltage source Vp. A diode D1 rectifies the current i(t) to represent blood flow in one direction only. Systolic capacitor Cs is analogous to the compliance (or elasticity) of the aorta during the systolic period. L represents the inertance of the blood, i.e., the ratio of the blood density to the blood vessel cross-sectional area. L may be assumed to be a constant because the effect of area variation is small.

During the diastolic portion of the cardiac cycle, the equivalent circuit model 10 is modified by replacing capacitor Cs with the parallel combination of diastolic resistance $R_D$ and diastolic capacitor $C_D$ between terminals 12 and 13. The arterial compliance is thus modelled as a piecewise linear capacitance with a value of Cs during systole and $C_D$ during diastole. $R_D$ is analogous to the peripheral arterial resistance during diastole. The model thus assumes a lossless system during systole represented by an LC "charge pump" circuit.

Figure 3:
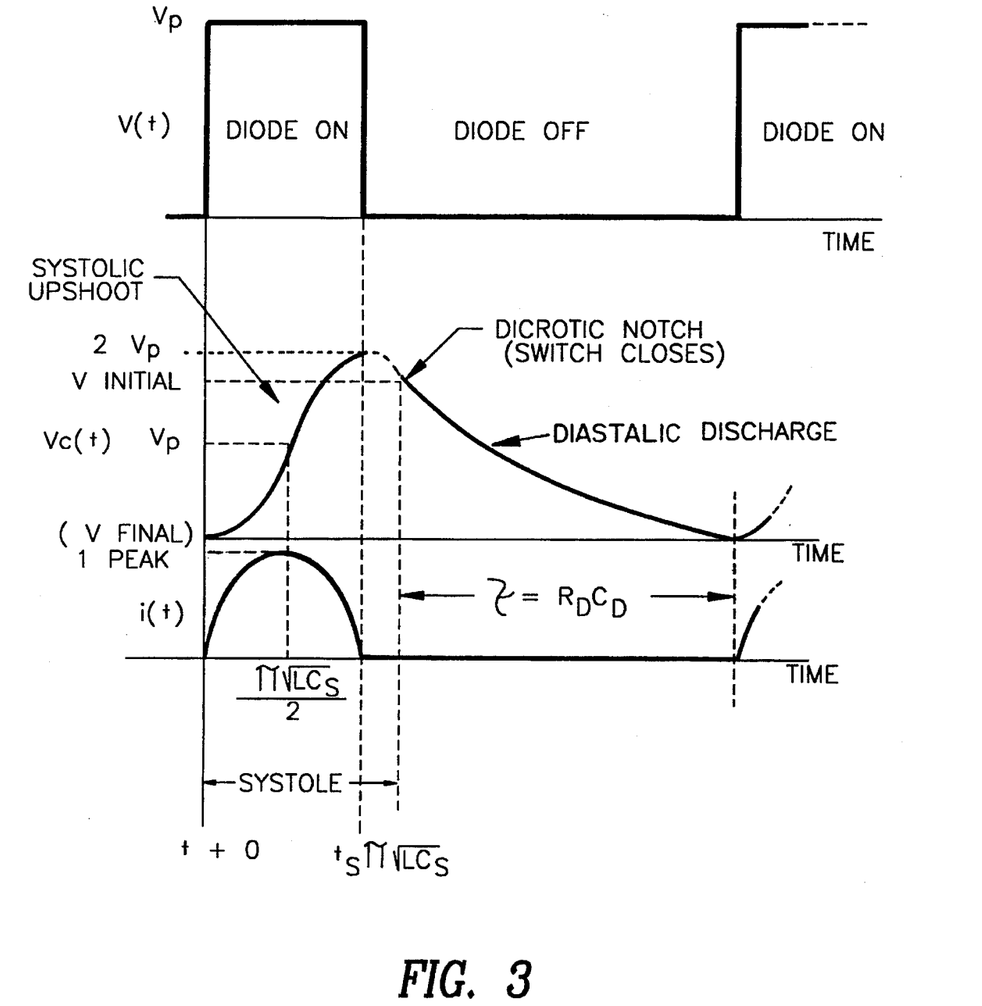
FIG. 3 shows theoretical voltage and current waveforms based on the LICO circuit model representative of arterial pressure and blood flow from the heart to the aorta.

At the start of systole, switch S closes (which corresponds to the aortic valve opening), thus providing a step input voltage Vp to the LC charge pump circuit (See FIG. 3). The step voltage Vp corresponds to a step input driving pressure from the left ventricle to the aorta. Because a lossless system is assumed during systole, the loop current i(t) flowing through the elements is an undamped sinusoid. This is illustrated in FIG. 3, which shows i(t) as the top half of a sine wave between the time t=0 when s closes and the time ts when Vc(t) reaches a maximum. It is noted here that while the start of systole is conventionally defined as the time when the mitral valve closes, it is defined herein for convenience as the time when the aortic valve opens. Moreover, it is seen that the diode $D_1$ is necessary in the equivalent circuit, in addition to the switch S, to prevent an equivalent negative current flow during the time period from $t_s$ to the end of systole.

The circuit model 10 is used to estimate blood flow in the following manner. An arterial pressure pulse waveform can be measured at various sites, including the carotid, femoral, and brachial A-line pulse, the latter of course being a generally undesirable invasive measurement. The arterial pressure waveform corresponds to the capacitor voltage waveform $V_c(t)$. The coordinates $V_c(t=0)$ and $V_c(t=\pi(LC)^{0.5})$ are extracted from the pressure pulse, where $t=\pi(LC_s)^{0.5}$ corresponds to the time of the rise of the voltage waveform $V_c(t)$. The peak or average current can be calculated with the following equations. The systolic charging time $t_s$ is measured from the foot to the peak of the pressure pulse and is used to solve for the capacitance $C_s$ as follows:

$$t_s = \pi(LC_s)^{0.5} \tag{1}$$

where L=1.0H
$C_s$=systolic arterial capacitance (Farads)
$t_s$=foot to peak time (sec).
The capacitor voltage waveform is given by $$V_c(t) = V_p \cos[(LC_s)^{-0.5}t] + V_p \tag{2}$$

where Vp=(voltage corresponding to max-min pulse pressure)/2
t=time during systolic charging.
The loop current is given by $$i(t) = (V_p/[(LC_s)^{0.5}]) * \sin[(LC_s)^{-0.5}t] \tag{3}$$

and $$i_{peak} = V_p/[(L/C_s)^{0.5}]. \tag{4}$$

If we substitute $$C_s = t_s^2/\pi^2 L, \tag{5}$$

Then, $$i_{peak} = V_p(t_s/(\pi L)). \tag{6}$$

The average flow can then be calculated from the peak flow from the time averaged current value over the length of the cardiac cycle. It is noted here that, for simplicity, the above equations assume that the pressure at t=0 represented by "$V_{final}$", is zero. In actuality, the pressure at this time is finite and thus, it is the systolic to diastolic pressure differential that is being modelled by $V_c(t)$. The minimum systolic pressure, Psys,min and maximum systolic pressure, Psys,max are measured and converted to corresponding voltages wherein (Psys,max–Psys,min) in mmHg is equivalent to 2Vp in volts.

The analogy between the electrical and physiological parameters is summarized in Table 1. Once compiled, the electrical parameters are readily converted into the corresponding hemodynamic parameters from the unit conversions shown to arrive at a measure of the desired cardiovascular parameter. Thus current is converted to blood flow in L/min, capacitance to compliance in mL/mmHg and so on.

TABLE 1

| Electrical | Physiological Unit | (hemo-dynamic) | Conversion Factor |
|---|---|---|---|
| voltage, V[volts] | Pressure, P | mmHg | 1 V ←→ 1 mmHg |
| charge, Q[coulombs] | volume, V | mL | .133L = 1.0 coulomb |
| current, i[amperes] | blood flow, Q | Liters/min | 1 A ←→ 8.0 L/min |
| resistance, R[ohms] | resistance, R' | mmHg-min/L | 8Ω ←→ 1 mmHg-min/L |
| capacitance, C[farads] | compliance, C' | mL/mmHg | 7500 μF ←→ 1 mL/mmHg |
| inductance, L[henrys] | inertance, L' | Kg/m⁴ | 1 H ←→ $10^6$ Kg/m⁴ |

The selection of L=1.0H (corresponding to inertance of $1.0 \times 10^6$ kg/m⁴) is approximately satisfactory for the carotid data, but may be invalid for the femoral and brachial artery data. The assumption that the inductor is fixed is based on the observation that the effect of area change is small, and the blood inertance equals the ratio of blood density to vessel cross-sectional area (for a distributed inertance). A value of L=$1.0 \times 10^6$ kg/m⁴ has been derived using nominal values for the human aorta. This lumped value is determined by the formula $$L = pl/A, \tag{7}$$

where p=blood density (gm/cm³)
l=vessel length (cm)
A=vessel cross-sectional area (cm²).
To find the diastolic capacitance $C_d$, the time constant of the diastolic decay of the pressure waveform is found. The start of the decay is defined at the dicrotic notch, or the end of systole. The decay continues throughout diastole until the beginning of the next systolic upshoot. The time constant, τ, is found as:

$$V_{final} = V_{initial} e^{-t/\tau} \tag{8}$$

where the initial voltage value represents the end systolic pressure Pes, and the final voltage value represents the end diastolic pressure Ped. The physiological analog for this relationship is:

$$P_{ed} = P_{es} e^{-t/\tau} \tag{9}$$

where: $P_{ed}$=end diastolic pressure, [mmHg]
$P_{es}$=end systolic pressure, [mmHg]
τ=time constant, [sec].
Using this time constant, the diastolic capacitance can be found using the diastolic resistance $R_d$:

$$C_d = \tau/R_d \tag{10}$$

where the diastolic resistance is found as the ratio of the mean pressure in diastole, $P_d$, to the mean flow in diastole, $Q_d$:

$$R_d = \frac{P_d}{Q_d}. \tag{11}$$

The mean flow in diastole, $Q_d$, is assumed to be equal to the amount of blood ejected in systole averaged over the entire diastolic period. This is determined by RMS averaging of systolic current i(t) over the diastolic period. The mean diastolic pressure is the average of the beginning diastolic pressure, determined from $V_{initial}$, and the end diastolic pressure, determined from $V_{final}$. Cardiac output in Liters/minute may then be determined by multiplying $Q_d$ by the heart rate in beats/minute.

Figure 4:
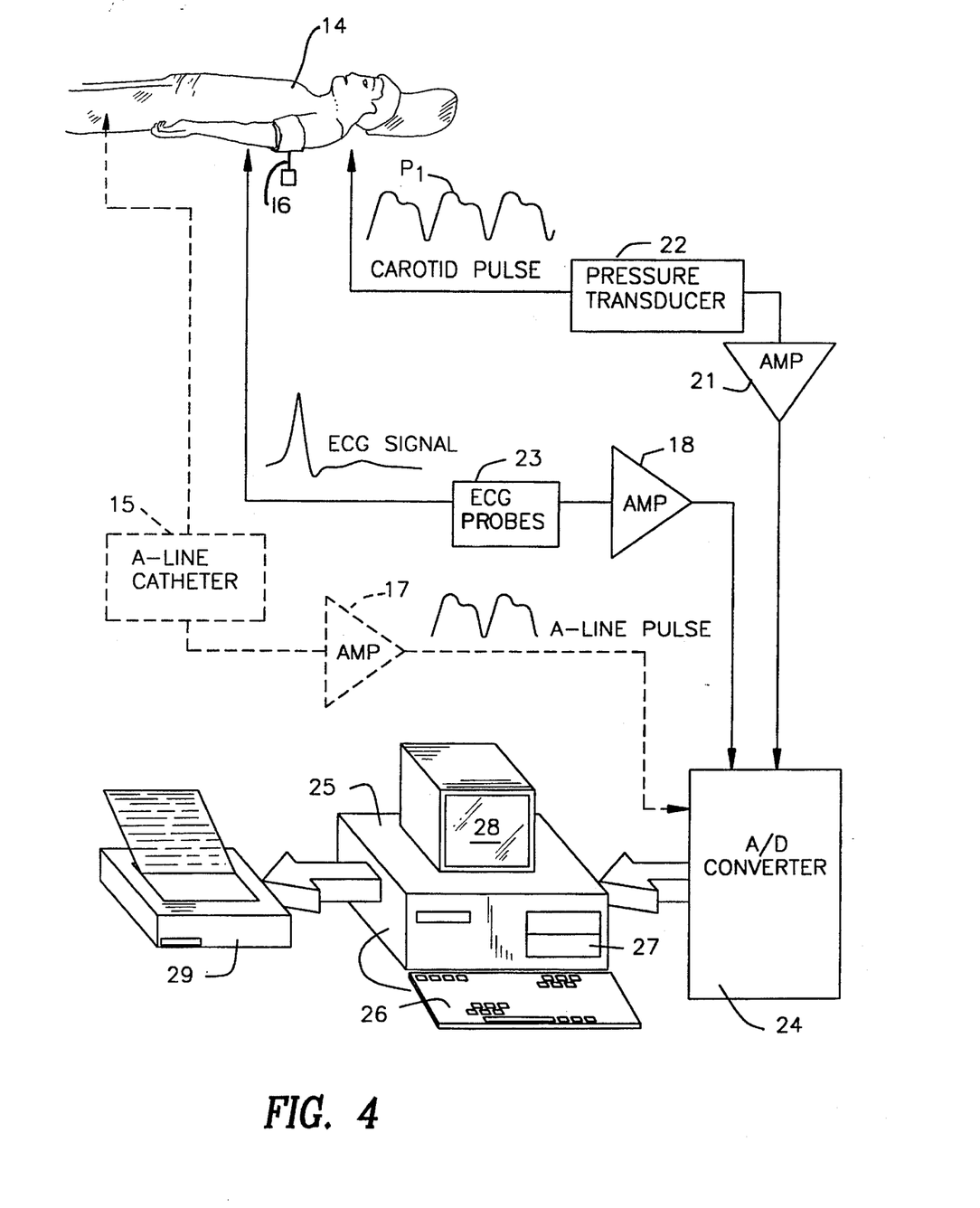
FIG. 4 shows an apparatus for measuring cardiovascular system parameters according to the present invention.

Having thus discussed the theoretical underpinnings of the first embodiment of the invention, physical implementation of the arterial system measurement will now be described. Referring to FIG. 4, a noninvasive pressure transducer 22 is employed to convert externally sensed arterial pulse contour perturbations to correspondingly shaped time-varying electrical waveforms. Pressure transducer 22 is preferably adapted to be placed in proximity to the carotid pulse of a living subject 14 in close contact with the subject's skin. The pressure transducer 22 is preferably of a piezo-electric transducer type and provides output signals to an appropriate filter/amplifier circuit 21 suitable for interfacing with A/D converter 24. It should be recognized that the proper positioning of the pulse transducer 22 requires knowledge of the location of the carotid artery. However, by providing the visual display screen 28 in connection with computer 25 (as is customary), it is possible for a health care professional to position the transducer 22 and, by observing the appropriate position on the patient 14 which results in substantially maximum pulse waveforms appearing on the display screen 28, to produce repeatable and acceptable output signals from transducer 22. An ECG signal from the patient 14 is measured using ECG probes 23 coupled to another amplifier/filter circuit 18, with the amplified ECG signal provided to A/D converter 24.

It should be noted that the output waveforms, upon being sensed by transducer 22, are not calibrated in terms of absolute pressure. In order to provide such calibration, noninvasive measurements of maximum systolic and maximum diastolic pressures of a subject are made. It has been determined experimentally that a sufficiently accurate amplitude calibration of the transducer 22 output may be provided by making use of a pressure cuff sphygmomanometer 16. Other external pressure measuring devices of similar or greater accuracy may also be employed for this purpose. The absolute systolic and diastolic pressure values measured by the cuff 16 are provided to the computer 25 either manually or automatically. This is done immediately preceding the pulse contour measurements and may also be repeated immediately afterwards as a calibration check.

The time-varying electrical waveforms produced by the transducer 22 are provided to an A/D converter 24 where they are digitized at a sampling rate of about 1 KHz. The digitized samples are provided to the computer 25 where they are stored as data to enable algorithms stored therewithin to compute the cardiovascular system parameters.

It should be understood that, instead of measuring a carotid pulse contour, a pulse contour from an A-line catheter 15, if available, may alternatively be utilized to determine the cardiovascular system parameters according to the invention. This is an invasive technique, of course, and should be avoided if possible. If available, the measured A-line pulses are likewise amplified and filtered by an amplifier/filter circuit 17, and then provided to the A/D converter 24.

Figure 5:
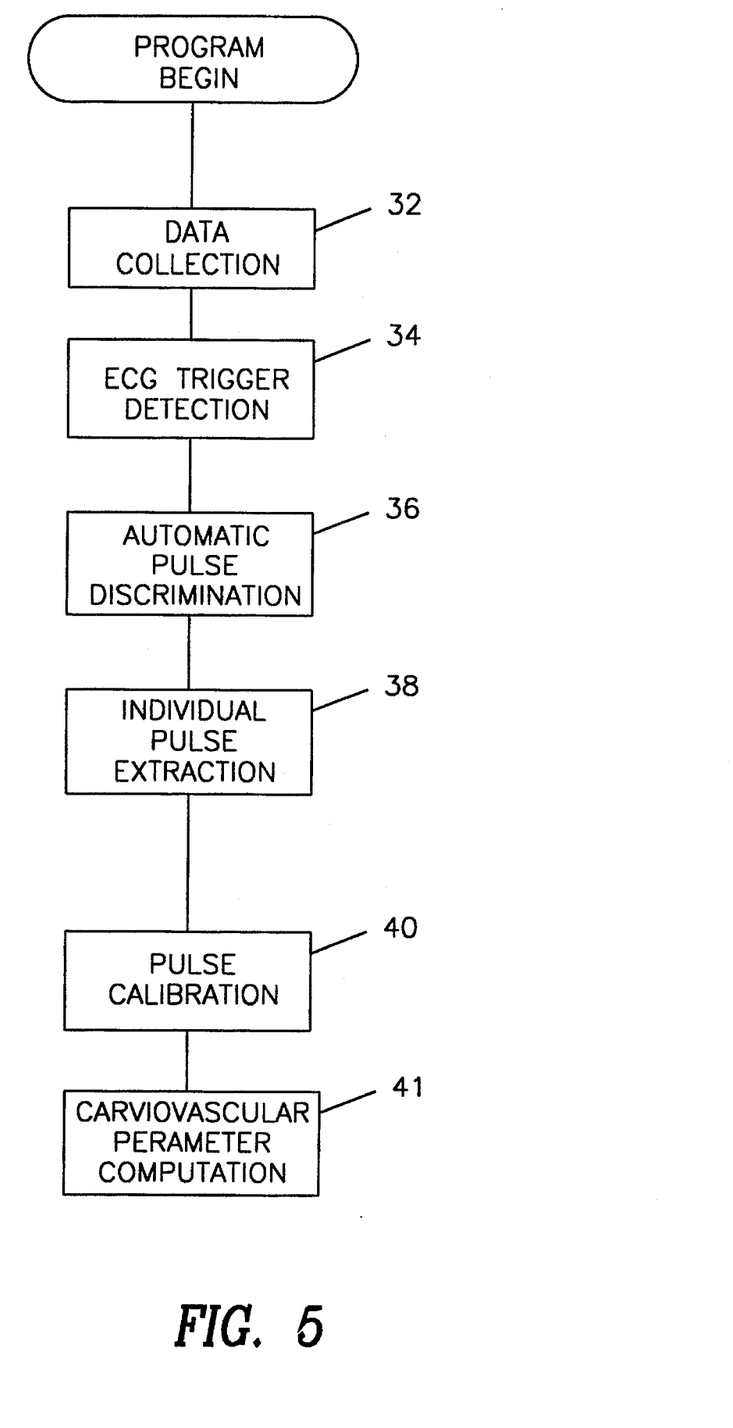
FIG. 5 is a software flow diagram showing a sequence of routines to measure cardiovascular system parameters according to the invention.
Figure 6:
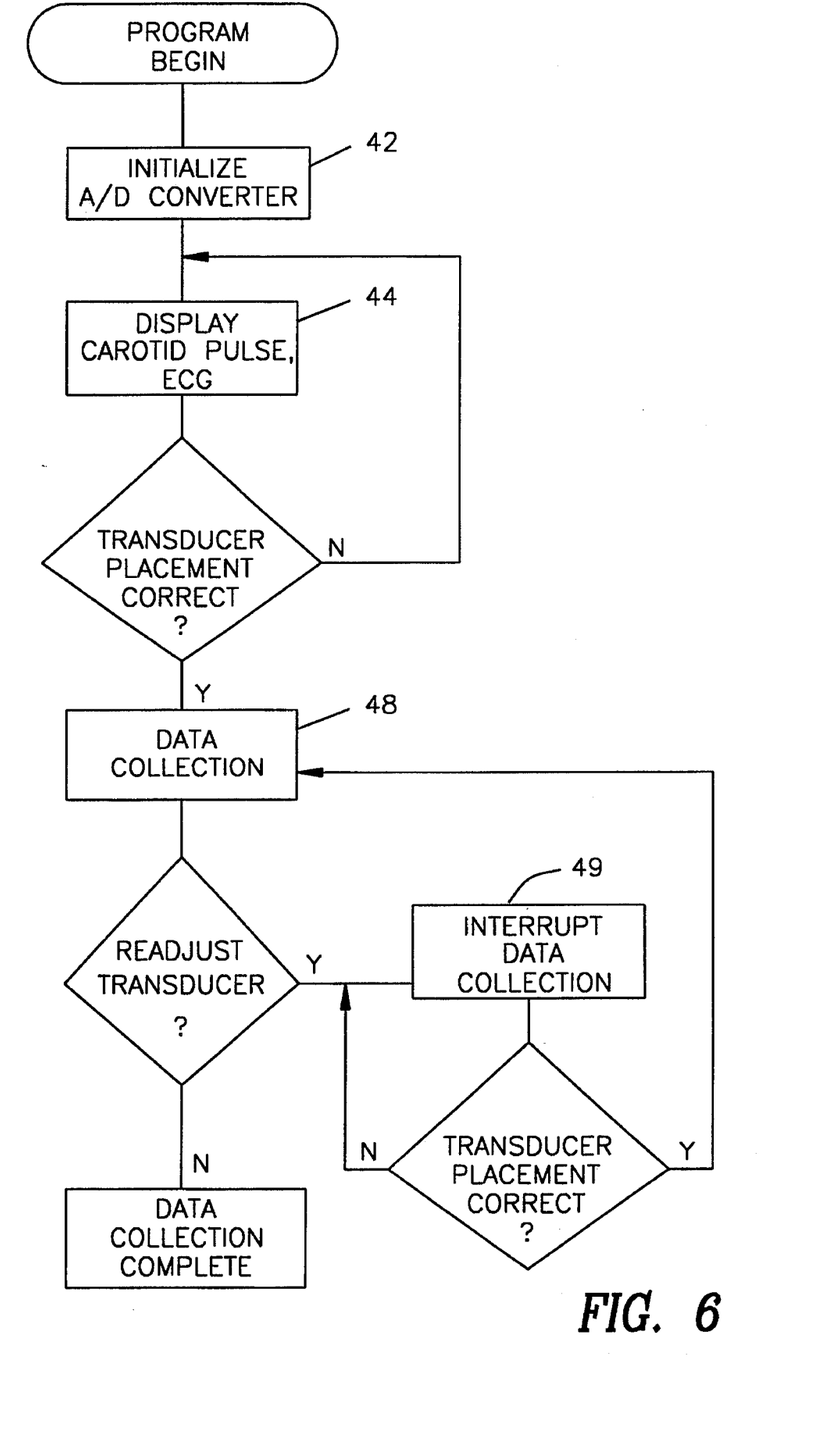
FIG. 6 is a software flow diagram of the data collection routine of FIG. 5.

The software used to implement the invention is made up of a group of programs or routines which, for example, may be written in Borland C/C++, BASIC, and so on. Once the pulse transducer 22 and ECG probes 23 are positioned on the patient, the program is commenced by the user via keyboard 26. Referring to FIG. 5, a data collection routine 32 is initiated upon the start of the program. This routine 32 controls all aspects of data collection for at least two channels of data—the carotid pulse waveform data and the ECG signal data. The software flow diagram of routine 32 is shown in FIG. 6. An initialize routine 42 first initializes the A/D converter 24 for the two channels of input data, each sampled at about 1 KHz. When initialization is complete, a display routine 44 allows the digitized carotid pulse and ECG waveforms to be displayed on the display 28. A printout of the waveforms can also be provided via printer 29. In this mode, the operator checks for proper placement of the transducer 22 by re-positioning it while viewing the display for a substantially maximum signal strength of the carotid waveform. Once transducer placement is correct, the user presses a key as directed by the program and a data collection routine 48 is commenced. At this time, up to one minute of continuous stream data will be stored within the computer 25 hard drive or on a floppy disk 27. The graphic display 28 is still active during this time to allow the operator to supervise the data collection. If the waveforms observed on the display degrade, a data interrupt routine 49 allows the operator to interrupt the data collection by depressing a key as instructed. The transducer or ECG probes may then be readjusted while the operator views the waveforms. The appropriate key is then depressed to resume data collection.

The continuous data stream files collected are separated into individual pulse files in order to evaluate single cardiac pulses. The first step in this process is to determine where one pulse ends and the next pulse begins. The ECG data is collected for this reason. Once data collection is complete, or simultaneously with data collection, an ECG Trigger Detection Routine 34 searches for each QRS complex in the ECG data file to define the start and stop points of each cardiac cycle. Routine 34 facilitates this search by first differentiating the ECG waveform to sharpen the edges of the QRS complex. The ECG signal is generally filled with noise which may be falsely interpreted as a QRS complex, but differentiation enhances greater changes in slope or slew rate. This produces a signal with more salient QRS complexes which are easily detected by passing the signal through a software threshold comparator. A threshold value is computed by finding the average peak value in the file and the approximate top of the noise riding on the signal between QRS complexes. A value 50 percent between the peak and noise top is used as a threshold value, and all positive crossings of this value are interpreted as the start of a cardiac cycle.

Figure 7:
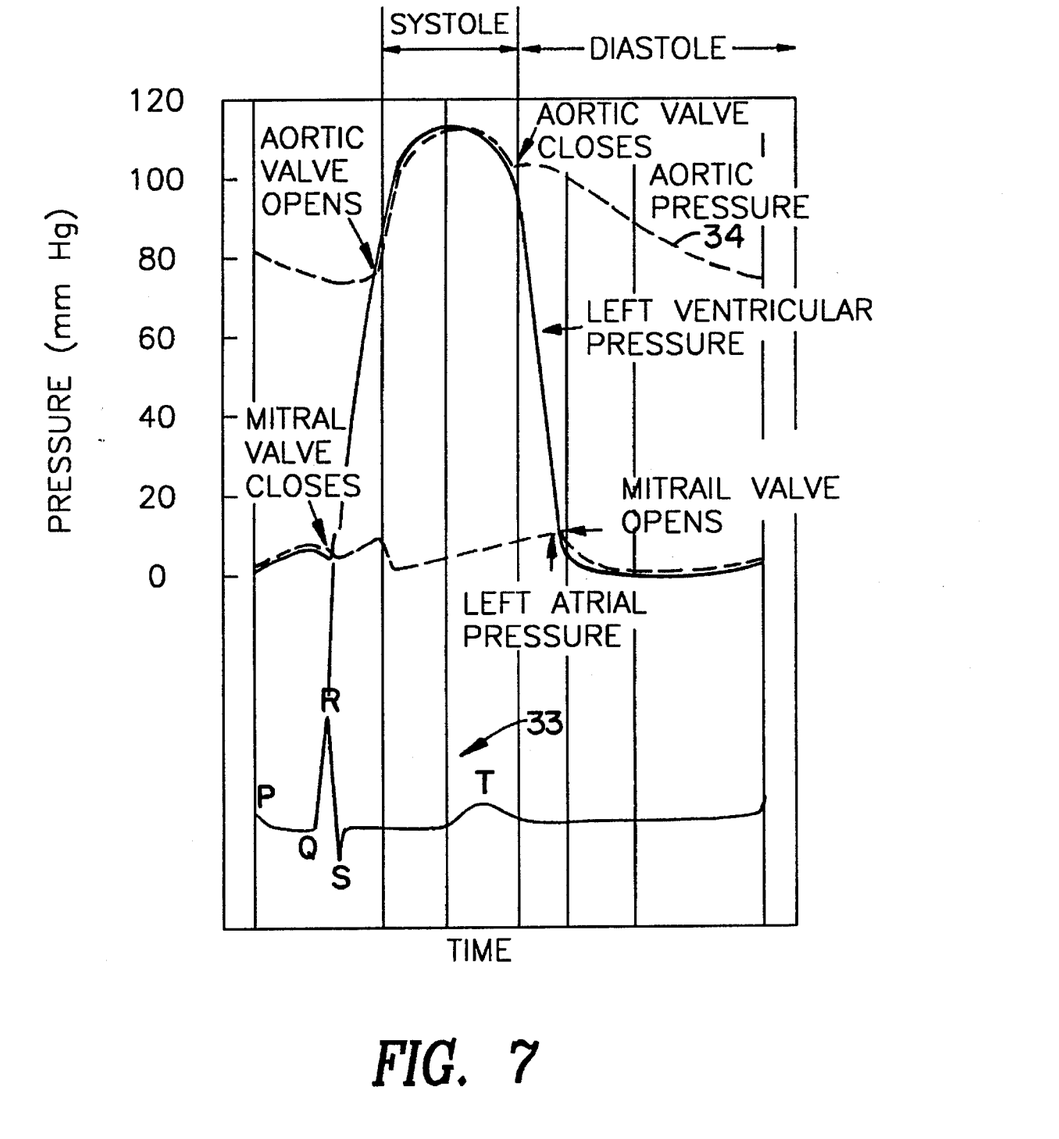
FIG. 7 shows waveform plots illustrating the timing relationship between the ECG pulse and the arterial pulse waveform.

The ECG Trigger Detection Routine 34 is adaptive; after a threshold is found, the file is evaluated and the number of cardiac complexes is counted. If the number represents a heart rate greater than 200 BPM or less than 40 BPM, then the process is reinitiated with a new threshold value. This new value is determined by the current threshold and complex number. If the number is too high, the threshold is increased to avoid the noisy spikes which are being interpreted as QRS complexes. The differentiation and thresholding are user-configurable from the DOS command line for troublesome cases. The routine 34 may also detect pacemaker spikes to avoid mistriggering on these signals. The output from routine 34 is an ECG trigger file which contains all zeros, except where a QRS complex was detected. In this location in the file, the pulse complex number is stored. The systolic and diastolic portions of the pressure pulse waveforms are then synchronized relative to the QRS complexes of the ECG pulse. This is illustrated in FIG. 7, which is provided here as background to show the timing relationship between the ECG pulse waveform 33 and the aortic pressure pulse waveform 34. See "Physiology", Berne, RM and Levy, MN, copyright 1993 by C.V. Mosby Co. It is noted that the aortic pressure waveform 34 is assumed to be essentially the same as the measured carotid pressure pulse waveform.

After the limits of the cardiac cycles have been defined, the carotid pulse waveform data stream files are separated into individual files. To improve arterial parameter prediction accuracy an Automatic Pulse Discrimination routine 36 is employed to extract only the superior pulses from the stream files. Routine 36 rejects poor pulses, noise and data corrupted by motion artifact. Pulses are evaluated as superior or inferior by considering several different parameters which define limitations on time and pressure points in the pulse. Criteria such as carotid pulse slope, saturation level, noise, waveshape, pulse magnitude and so on are used for the evaluation. If one or more of the criteria falls out of a predetermined range, the pulse is rejected as inferior. Otherwise, it is considered a good pulse and the pulse number with associated data is stored in an ASCII file for later use.

The good pulses are then extracted individually by means of a pulse extraction routine 38. Routine 38 reads the ASCII file created by the discrimination routine 36 and extracts the pulse numbers with digitized pulse and ECG waveform data stored therein. Following the pulse extraction, the individual pulse files may be displayed and recalibration of the individual pulses may be performed if the operator so desires. Once displayed, the user may select several predefined pressure and time points from the displayed carotid pulse using a mouse or the like. The user may select to recalibrate the particular pulse by means of a calibration routine 40. This may be desirable if, for example, the user visually determines that the highest (systolic) and the lowest pressure (diastolic) points on the pulse need to be redefined. This is sometimes necessary when the cuff pressure and the arterial line pressures (if taken) are different. The routine 40 also enables the user to change the contour of the pressure wave when the signal contains motion artifact or breathing modulation.

A cardiovascular parameter computation routine 41 computes cardiac output and arterial impedance parameters for each of the good pulses, whether or not recalibrated. The computed parameters can be averaged for several of the good pulses to arrive at the final predicted values for the patient. The computation is performed by using algorithms based on the LICO circuit model equations discussed hereinabove to compute Cs, Cd, Rd, Qd and so on.

Figure 8:
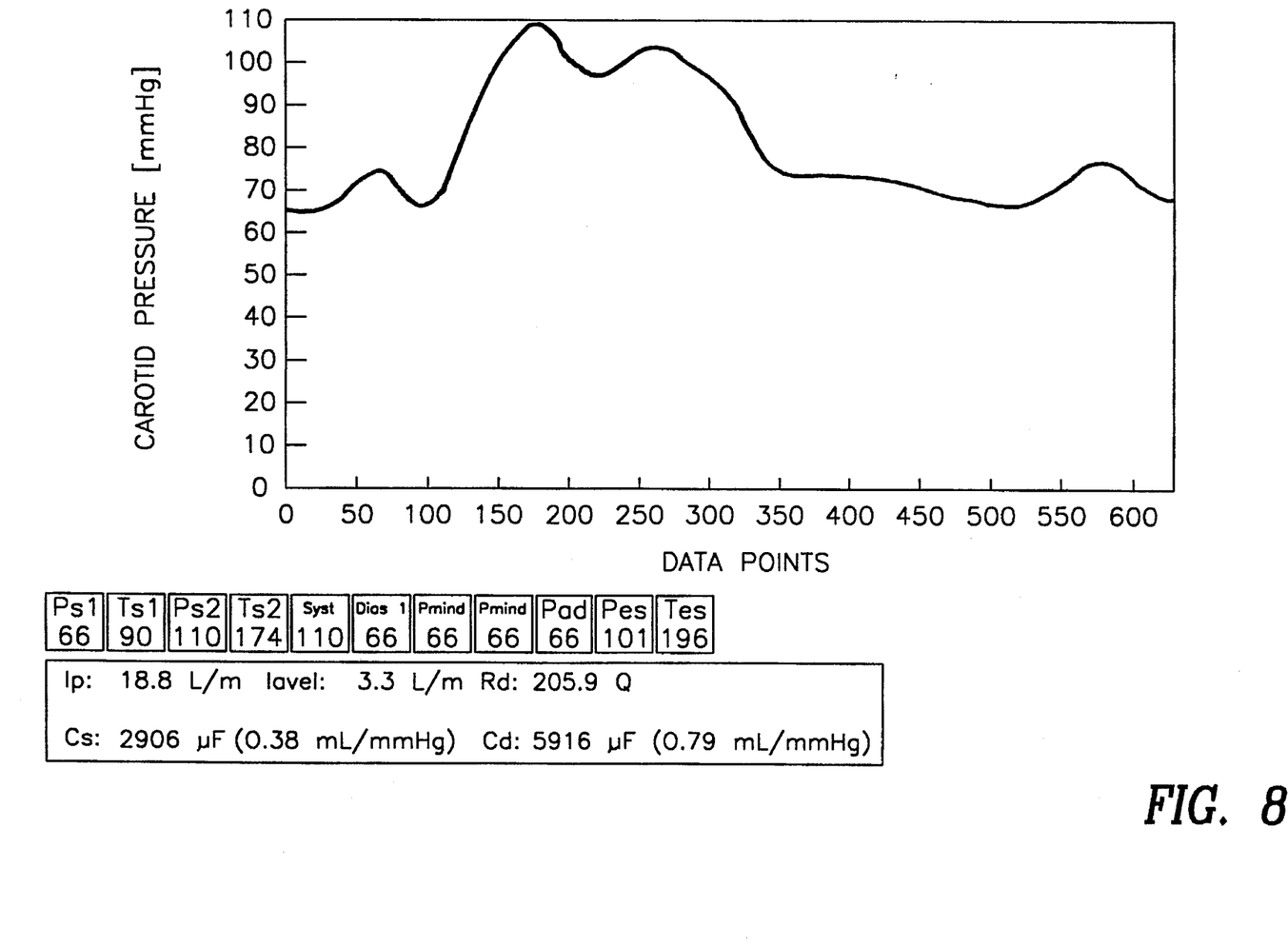
FIG. 8 shows an example of a measured arterial pressure pulse along with associated measured parameters.

Referring to FIG. 8, the graphics display for a typical pressure pulse is shown with the voltage waveform converted back to corresponding pressure units. The pressure at the beginning of systole Ps1, at time Ts1, and the maximum systolic pressure Ps2 at time Ts2 is determined. These values may be recorded for each carotid pulse using a computer mouse by manually moving cursors to the desired pressure and time points in response to computer prompts. Alternatively, the pressure and time points may be determined automatically by an algorithm as part of the computation routine 41 which searches for the minimum and maximum voltages of the waveform and automatically finds the desired pressure and time values at other points in the waveform. Exemplary values are shown beneath the graph in FIG. 8. In any case, the systolic capacitance Cs is computed from Ts1–Ts2 (i.e., ts, as discussed earlier). The blood flow according to i(t) is then computed from Cs, Ps1 and Ps2. The mean pressure in diastole, $P_d$ may be determined by integration averaging of the pressure values from the "end-systole" time, $T_{es}$ to the "end-diastole" time, Ted(which equals Ts1). Diastole resistance $R_d$ is then computed by finding $Q_d$ from i(t). $C_d$ is then determined from $R_d$ and $\tau$, i.e., $T_{es}-T_{ed}$.

Figure 9A:
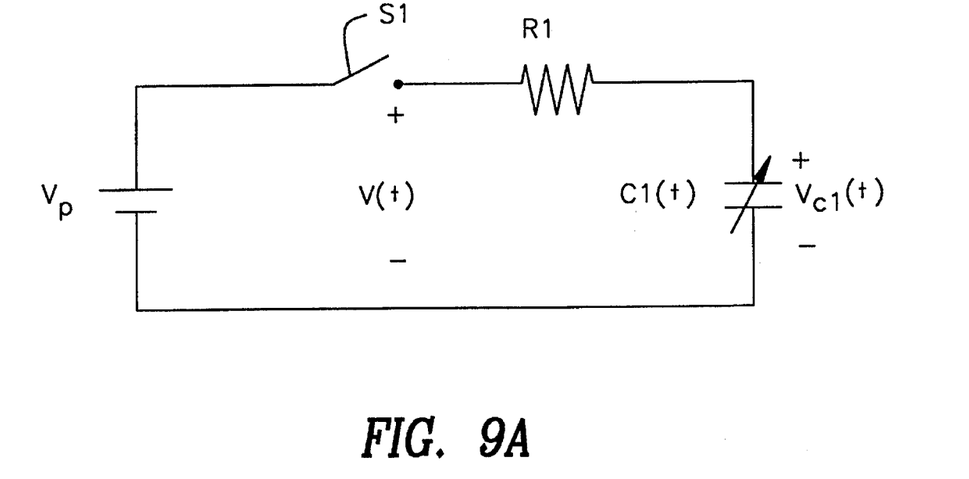
FIG. 9A is a first alternate equivalent circuit model used to compute a time varying arterial compliance according to a second embodiment of the invention.
Figure 9B:
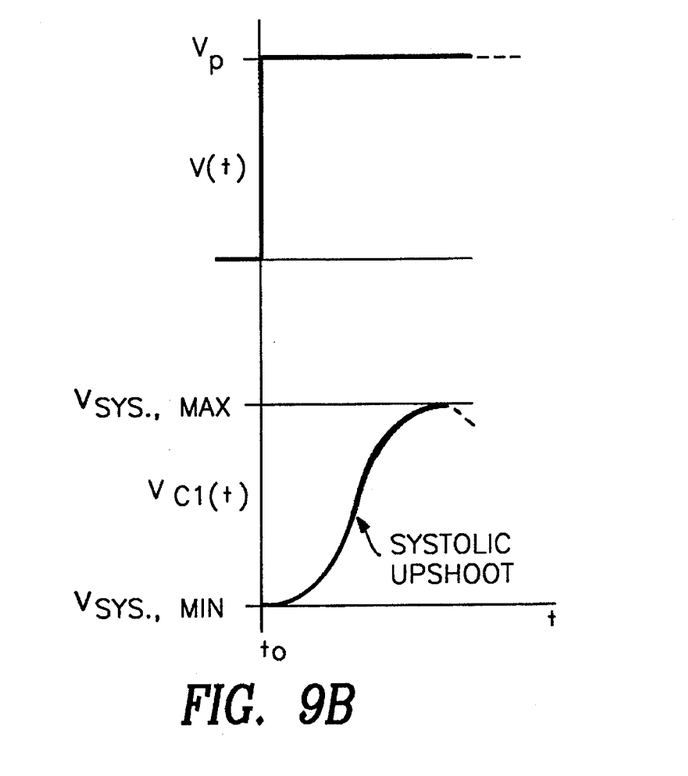
FIG. 9B shows voltage waveforms occurring in the circuit of FIG. 9A.

A second embodiment of the invention is now presented, which provides an alternate approach to measuring arterial compliance. This approach is based on the circuit model shown in FIG. 9A. The artery is modeled as a first order system with an input resistance R1 and time varying capacitance C1(t). As the driving pressure increases, the pressure waveform measured distally, P(t), corresponds to a voltage $V_{c1}(t)$ across the charging capacitor. The increase in driving pressure is represented as a DC voltage source Vp in series with a switch S1 that closes to begin systole and opens to end systole. The time constant for this system is $\tau(t)=R1C1(t)$, where the input resistance R1 may be assumed to be a constant of 1.25 ohms, and the compliance, C'(t), represented by C1(t), is time-varying. Compliance values at each time t are computed by first defining the start and stop time indices of the "charging" pressure waveform P(t), represented by $V_{c1}(t)$ as shown in FIG. 9B. For all C'(t), the start point is the foot of the pressure waveform at $t=t_o$ and the final charging value is the maximum systolic pressure, Psys,max which corresponds to the maximum voltage, Vsys, max. The stop point is simply P(t), or the pressure at that time in the systolic upshoot. The time-varying compliance in mL/mmHg over the charging cycle is computed as:

$$C'(t)=(t-t_o)\times133.322/(R1\times1\ n((P(t)-Psys,max)/(Psys,max-Psys,min))) \qquad (12)$$

where:
P(t)=arterial pulse pressure vs. time during systole
R1=input resistance of the arterial segment
$t_0$=time of the foot of the systolic upshoot
Psys,min=pulse pressure at beginning of systole
Psys,max=maximum systolic pulse pressure
133.322=conversion from [sec/ohm] to [mL/mmHg] for capacitance values.

It is noted that the unit conversions expressed in Table 1 are also applicable to equation (12).

Thus, from a measure of the arterial pulse pressure as a function of time, the time varying arterial compliance C'(t) can be readily determined. This may be accomplished by transducing the carotid or other arterial pulse waveform using the equipment set-up of FIG. 4 in substantially the same manner as with the LICO based measurements described above. The LICO software would have to be modified to allow computation of C'(t) according to the above equation. The desired pressure vs. time values may be extracted using a computer mouse or automatically with an additional algorithm, as one skilled in the art would understand. An ECG is still preferably taken and provided to the computer 25 via A/D converter 24 to facilitate the identification of the systolic and diastolic portions of the pressure wave. As with the LICO based method, the pulse pressure and ECG data is organized into individual files each representative of a single cardiac cycle for analysis of the compliance C'(t) during the systolic portion of the individual cycles.

Figure 10:
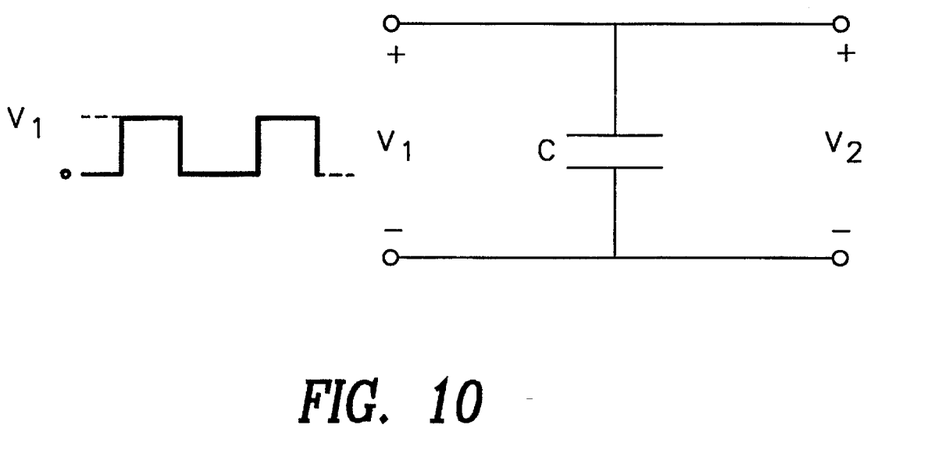
FIG. 10 is a second alternate equivalent circuit model used to compute cardiovascular system parameters according to a third embodiment of the invention.

A third embodiment of the invention, which encompasses a second alternate approach for measuring cardiovascular system parameters is now presented. With this embodiment, cardiac output can be determined from a simple measurement of heart rate and blood pressure without resorting to a relatively complicated measurement and analysis of the arterial pulse pressure waveform. The approach is based on the unmodified Windkessel circuit model. Referring to FIG. 10, the Windkessel capacitance circuit consists of a single shunt capacitor C. Capacitor C represents a single lumped arterial compliance C'. During systolic contraction, the left ventricle drives a stroke volume into the aorta. The walls of the aorta stretch elastically during systole, to temporarily store the blood received, akin to a capacitor storing a charge. Then, during diastole, the blood is issued to the periphery in an exponentially decaying fashion, which is akin to a capacitor discharging. The driving pressure from the heart to the aorta during systole is akin to a pulsed input voltage with a peak magnitude of V1. The blood stored by the aorta during systole is akin to stored charge which produces a charging voltage V2 across the capacitor C. A lossless system is assumed during systole.

To derive an equation for computing cardiac output (CO) using this approach, we start with the definition of cardiac output, to wit, $$CO(L/min)=HR(beats/min) \times SV(liters). \qquad (13)$$

Since the heart rate (HR) is easily measured, the solution of this equation for CO is reduced to obtaining the stroke volume (SV). In the analogous electrical system, volume SV (liters) corresponds to charge Q (Coulombs) according to the conversion: 0.133 liters=1 Coulomb. Substituting this into the above equation, $$CO(L/min)=HR(beats/min) \times Q(Coulombs) \times 0.133 \; Liters/Coulomb. \qquad (14)$$

The equation for charge on a capacitor is $$Q(Coulombs)=C(Farads) \times V(Volts) \qquad (15)$$

where V is the potential difference (V+−V−) between the oppositely charged plates of a parallel plate capacitor. Substituting in for Q, $$CO(L/min)=HR(beats/min) \times C \; (Farads) \times V(Volts) \times 0.133 \; liters/Coulomb. \qquad (16)$$

The process of charging a capacitor C involves the transfer of electrical charge Q from a plate at a lower potential to a plate at a higher potential. When a battery is connected to a parallel plate capacitor, it supplies the potential difference which separates the charge. In the hydraulic circulatory system, the stroke volume ejected by the ventricle is stored by the compliant aorta. The volume of blood stored is determined by the pulse pressure (systolic minus diastolic pressure). The Pulse Pressure (PP in mmHg) is analogous to the potential difference V (Volts) according to the conversion 1 mmHg=1 Volt. Substituting in, we have $$CO(L/min)=HR(beats/min) \times C(Farads) \times PP(mmHg) \times 0.133 \qquad (17)$$

or equivalently, $$CO(L/min)=f_{hr}(Hz) \times C(Farads) \times PP(mmHg) \times 8.0 \qquad (18)$$

where $$f_{hr}(Hz)=HR(beats/min)/60(sec/min) \qquad (19)$$

Note that 8.0 L/min=1.0 Ampere, since $$Ampere=Coulomb/sec=(Farad \times Volt)/sec=(Farad \times mmHg)/sec=Hz \times Farad \times mmHg. \qquad (20)$$

If an accurate estimate of the capacitance C can be provided, cardiac output can then be predicted on a given patient from a simple heart rate and cuff pulse pressure measurement. By taking measurements of cardiac output using a recognized standard method such as thermodilution or Doppler ultrasound, in a conventional manner on a large number of patients, along with pulse pressure and heart rate data, regression equations for the capacitance C can be derived. These regression equations can then be used for the noninvasive determination of cardiac output on new patients. The equations according to the invention were derived using numerical optimization techniques from thermodfiution data on approximately 200 patients. Five different regression equations for C were derived and are listed in Table II.

The equations are listed as equations I to V in the order of increasing accuracy. The linear equation I is the least accurate and equation V wherein C is a function of height, weight and age is the most accurate. Equations I to V are only valid for adults.

It is noted that the thermodilution method has became the standard clinical method for measuring cardiac output. It is generally considered by those skilled in the art to be accurate to within +/−20%. The thermodilution technique for cardiac output estimation is based upon the change in blood temperature over time measured by a thermistor at the tip of a catheter in the pulmonary artery. This temperature change is brought about by the injection of a bolus of cold saline into the fight atrium. The cold saline mixes with venous blood and causes the temperature of the blood to decrease about 0.5° to 1.5° C.

TABLE II

| Equation Number | Equation Type | C(uF) |
| --- | --- | --- |
| I. | linear | 11,359 − 70 *PP |
| II. | polynomial | 12,373 − 97 *PP + 0.2 *PP$^2$ |
| III. | multiple (PP,h) | −2,439 − 75 *PP + 82 h |
| IV. | multiple (PP,h,w) | −1,887 − 75 *PP + 75 h + 7.5 w |
| V. | multiple (PP,h,w,a) | −2,071 − 73 *PP + 80 h + 5.6 w − 8.9 a | notes:
PP (mmHg) = pulse pressure
w (Kg) = weight
h (cm) = height
a (years) = age The extent of cooling is inversely proportional to cardiac output. Thermodilution is an indicator dilution method, but no blood needs to be withdrawn. However, it does require the surgical placement of a catheter which is pushed through a vein in the neck, through the right atrium and into the pulmonary artery. Examples of thermodilution techniques can be found in an article by M. Yelderman, entitled "Continuous Measurement of Cardiac Output with the Use of Stochastic System Identification Techniques", J. Clin. Monit., 6:322–332, 1990, the content of which is incorporated herein by reference.

Figure 11:
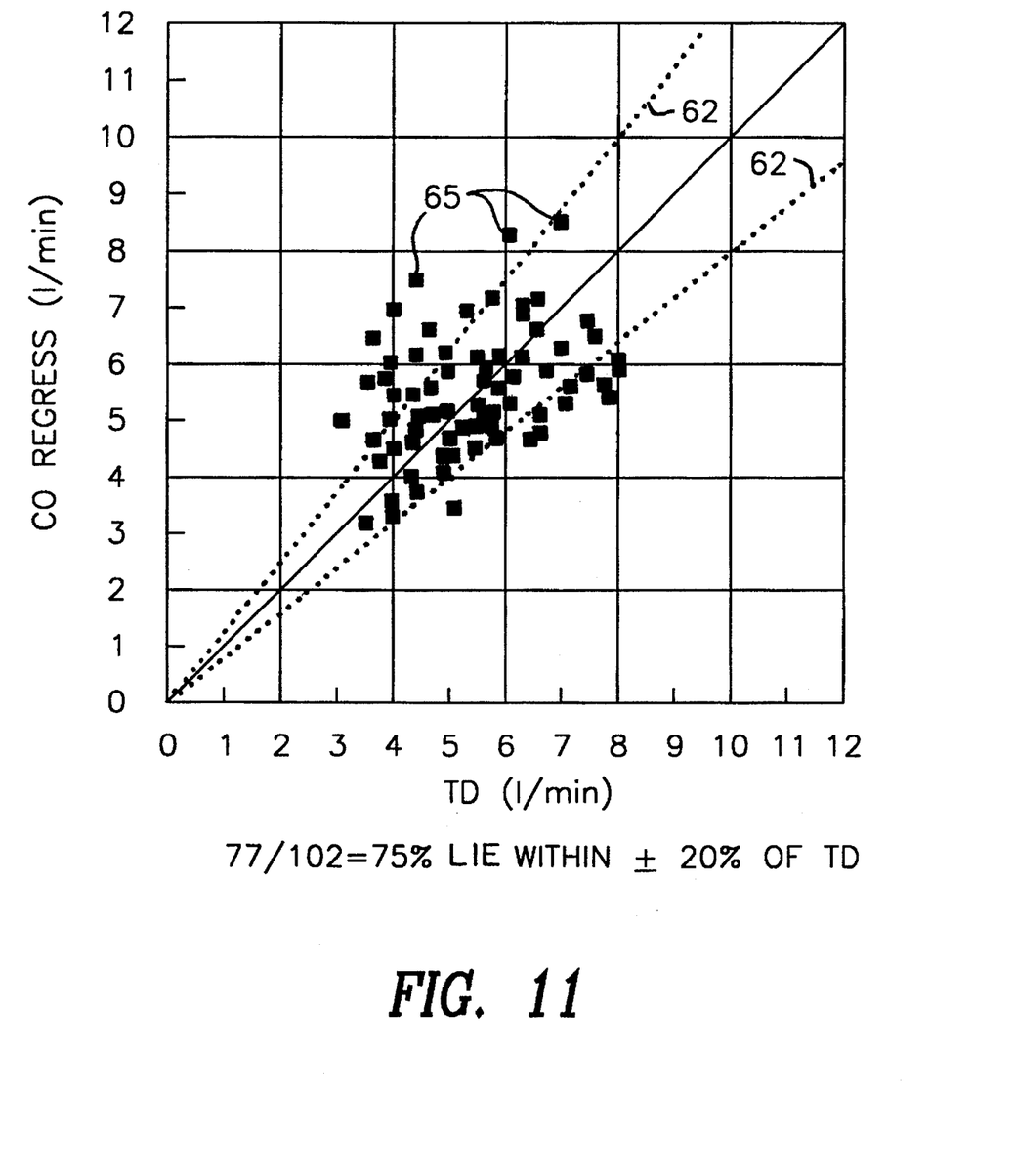
FIG. 11 shows measured data of cardiac output according to the third embodiment of the invention.

Referring to FIG. 11, a comparison of cardiac output (CO) measurements were performed on 102 patients using both a thermodilution technique and the noninvasive Windkessel capacitance model technique according to the invention. Regression equation III of Table II was used to compute the capacitance C. The dotted lines 62 designate a +/− 20% window to take into account absolute thermodilution accuracy as is known by those familiar with thermodilution. The data squares 65 represent cardiac output data points computed using equation III from heart rate and pulse pressure data. Each square 65 is plotted vs. the CO value for a given patient that was also measured using thermodilution. It is seen that 77 out of 102 data points, or 75% lie within the thermodilution accuracy window. A similar accuracy can be achieved using the other listed equations of Table II. Thus the advantage of this latter embodiment of the present invention is readily apparent in that cardiac output measurement accuracy substantially close to that of thermodilution is achieved noninvasively with a simple heart rate and pulse pressure measurement.

Moreover, an experimental comparison between cardiac output measurements based on the LICO circuit model-analysis discussed hereinabove, with thermodilution data taken on the same patients also shows a positive correlation between the measurements. The advantage of the noninvasive CO LICO based measurement is thus also readily apparent.

It should be understood that the embodiments described herein are merely exemplary and that a person skilled in the art may make many variations and modifications to the described embodiments utilizing functionally equivalent components or steps to those described. For instance, while the arterial pulse pressure waveform measurements have been described as being taken noninvasively, one may also take invasive pressure waveform measurements such as via the A-line if so desired, to determine cardiovascular system parameters as taught herein. Moreover, instead of utilizing a thermodilution standard to derive equations for the noninvasive measurement of arterial compliance from the unmodified Windkessel model as disclosed herein, one could use other suitable cardiac output standards such as Doppler ultrasound. All such variations and modifications are intended to be included within the scope of this invention as defined by the appended claims.

What is claimed is:

1. An apparatus for measuring cardiovascular system parameters of a living subject, comprising:

means for modelling the parameters of the living subject with a lumped element electric circuit model analogous to the living subject's cardiovascular system, said circuit model including a systolic capacitor analogous to arterial compliance during systole;

first transducer means for sensing a time varying arterial pressure pulse waveform from the living subject and converting said pressure pulse waveform to an electrical voltage waveform having voltages corresponding to systolic and diastolic arterial pressures of the subject;

means for computing the value of said systolic capacitor from a measurement of an elapsed time between two voltage levels within a portion of said voltage waveform corresponding to systole, according to a predetermined criteria; and means for computing the cardiovascular system parameters from said capacitor value.

2. The apparatus according to claim 1 wherein said means for computing the value of said systolic capacitor computes said systolic capacitor value from the following equation:

$$C_s = t_s^2 / \pi^2 L$$

where $C_s$ is the systolic capacitance; one of said two voltage levels is a low voltage level, the other of said two voltage levels is a high voltage level, $t_s$ is said elapsed time between said low and high voltage levels; and L is a predetermined inductance value representative of inertance of blood; and wherein said means for computing the cardiovascular system parameters computes said arterial compliance during systole from said systolic capacitance.

3. The apparatus according to claim 2 wherein the cardiovascular system parameters include average blood flow from the living subject's heart, and further including:

means for computing a loop current representative of blood flow from the living subject's heart to the living subject's aorta during systole, said loop current defined by the following equation:

$$i(t) = (V_p / [(LC_s)^{0.5}]) * \sin[(LC_s)^{-0.5} t]$$

where i(t) is the loop current, t is time; $V_p$ is one half of said high voltage level of said portion of said electrical voltage waveform corresponding to systole; and further including:

means for converting said loop current to a corresponding average blood flow value in the living subject by averaging said loop current over a single cardiac cycle.

4. The apparatus according to claim 3 wherein the cardiovascular system parameters also include mean blood flow in diastole from the living subject's heart, and further including:

means for determining a mean diastolic pressure Pd from said portion of said electrical voltage waveform corresponding to diastole;

means for computing said mean blood flow in diastole Qd, from said loop current averaged over said portion of said electrical voltage waveform corresponding to diastole; and means for computing arterial diastolic resistance Rd defined by the equation:

$$Rd = Pd/Qd.$$

5. The apparatus according to claim 4, further including:

means for determining another elapsed time between another low voltage level and another high voltage level of said portion of said electrical waveform corresponding to diastole, said another low voltage level corresponding to pressure at the end of diastole, said another high voltage value corresponding to pressure at the end of systole;

means for computing a diastolic capacitance value of said lumped element circuit model according to the equation:

$$Cd = \tau / Rd$$

where Cd is said diastolic capacitance value; $\tau$ is said another elapsed time; and Rd is said diastolic resistance; and wherein said means for computing the cardiovascular system parameters further includes means for computing a value of arterial diastolic compliance from said diastolic capacitance value.

6. The apparatus according to claim 1 further including:

means for identifying systolic and diastolic portions of said electrical waveform;

second transducer means for providing an ECG signal from the subject;

A/D conversion means coupled to said first and second transducer means for digitizing said electrical voltage waveform and said ECG signal;

processing means coupled to said A/D conversion means, for separating continuous data streams of said electrical voltage waveform and said ECG signal into a plurality of individual data files each representative of said pressure waveform and said ECG signal during one cardiac cycle, said data files being used to compute the cardiovascular system parameters of the living subject by said means for computing the cardiovascular system parameters, said processing means including means for searching for each QRS complex of said ECG signal to define start and stop points of each cardiac cycle; and display means coupled to said processing means for displaying said voltage waveform and said ECG signal one said individual data file at a time.

7. The apparatus according to claim 6 further including means for discriminating among voltage waveforms of said individual data files to selectively enable subsequent computation of cardiovascular system parameters on said voltage waveforms of said individual data files.

8. A method for noninvasively measuring cardiovascular system parameters of a living subject, comprising the steps of:

providing a lumped element electric circuit model analogous to the living subject's cardiovascular system for modelling the parameters of the living subject, said circuit model including a systolic capacitor analogous to arterial compliance during systole;

sensing a time varying arterial pressure pulse waveform from the living subject;

converting said pressure pulse waveform to an electrical voltage waveform having voltages corresponding to systolic and diastolic arterial pressures of the subject;

computing the value of said systolic capacitor from a measurement of an elapsed time between two voltage levels within a portion of said voltage waveform corresponding to systole, according to a predetermined criteria; and computing the cardiovascular system parameters from said capacitor value.

9. The method according to claim 8 wherein said step of sensing includes sensing said arterial pressure pulse waveform from the carotid artery of the living subject.

10. The method according to claim 8 wherein said step of sensing includes sensing an arterial A-line pressure pulse waveform from the carotid artery of the living subject.

11. The method according to claim 8 wherein said step of computing the value of said systolic capacitor includes:

providing a first equation:

$$C_s = t_s^2 / \pi^2 L$$

where $C_s$ is the systolic capacitance; one of said two voltage levels is a low voltage level, the other of said two voltage levels is a high voltage level, $t_s$ is said elapsed time between said low and high voltage levels; and L is a predetermined inductance value representative of inertance of blood;

computing the value of said systolic capacitor using said first equation.

12. The method according to claim 11 wherein said step of computing the cardiovascular system parameters from said capacitor value includes computing the arterial compliance during systole from said systolic capacitance.

13. The method according to claim 12 wherein the cardiovascular system parameters include average blood flow from the living subject's heart, and further including:

providing a second equation:

$$i(t) = (Vp/[(LC_s)^{0.5}]) * \sin [(LC_s)^{0.5} t],$$

where i(t) is the loop current which is representative of blood flow from the living subject's heart to the living subject's aorta during systole, t is time; Vp is one half of said high voltage level of said portion of said electrical voltage waveform corresponding to systole;

computing said loop current using said second equation; and converting said loop current to an average blood flow value in the living subject by averaging said loop current over a single cardiac cycle.

14. The method according to claim 13 wherein the cardiovascular system parameters also include mean blood flow in diastole from the living subject's heart, and further including:

determining a mean diastolic pressure Pd from said portion of said electrical voltage waveform corresponding to diastole;

computing said mean blood flow in diastole Qd, from said loop current averaged over said portion of said electrical voltage waveform corresponding to diastole;

providing a third equation:

$$Rd = Pd/Qd;\text{ and}$$

computing arterial diastolic resistance Rd using said third equation.

15. The method according to claim 14 further including the steps of:

determining a second elapsed time z between a second low voltage level and a second high voltage level of said portion said electrical waveform corresponding to diastole, said second high voltage level corresponding to pressure at the end of systole, said second low voltage value corresponding to pressure at the end of diastole;

providing a fourth equation:

$$Cd = \tau / Rd,$$

where Cd is said diastolic capacitance value; $\tau$ is said second elapsed time; and Rd is said diastolic resistance;

computing a diastolic capacitance value of said lumped element circuit model using said fourth equation;

computing a value of arterial diastolic compliance from said diastolic capacitance value.

* * * * *